(12) United States Patent
Suh (10) Patent No.: US 6,393,917 B1
(45) Date of Patent: May 28, 2002

(54) SYSTEM AND METHOD FOR ULTRASONIC IMAGE RECONSTRUCTION USING MODE-CONVERTED RAYLEIGH WAVE

(76) Inventor: Dong-Man Suh, Hanbit Apt. 119-1401 Oun-Dong Yusun-Gu, Taejon 305-755 (KR)

( * ) Notice: Subject to any disclaimer, the term of this patent is extended or adjusted under 35 U.S.C. 154(b) by 0 days.

(21) Appl. No.: 09/638,984

(22) Filed: Aug. 15, 2000

Related U.S. Application Data (60) Provisional application No. 60/149,054, filed on Aug. 16, 2000.

(51) Int. Cl.[7] .......................... G01N 29/06; G01N 29/10
(52) U.S. Cl. ........................................... 73/628; 73/602
(58) Field of Search .................. 73/597, 598, 599, 73/600, 620, 622, 624, 625, 627, 628, 602

(56) References Cited

U.S. PATENT DOCUMENTS

| | | | | |
|---|---|---|---|---|
| 4,174,635 A | * | 11/1979 | Olendorf | 73/606 |
| 4,299,128 A | * | 11/1981 | Gruber | 73/627 |
| 4,570,487 A | * | 2/1986 | Gruber | 73/624 |
| 4,658,649 A | * | 4/1987 | Brook | 73/598 |
| 5,760,904 A | * | 6/1998 | Lorraine et al. | 356/513 |

FOREIGN PATENT DOCUMENTS

EP 425765 A1 * 5/1991

* cited by examiner

Primary Examiner—Hezron Williams
Assistant Examiner—Rose M. Miller
(74) Attorney, Agent, or Firm—Lieberman & Nowak LLP (57) ABSTRACT

A system and method for image reconstruction of defects in solid materials based on mode-converted Rayleigh waves (MCRW). The system and method isolate the Rayleigh wave signals from the specular reflection signals although the Rayleigh wave signal amplitude is much weaker than the specular signal. It was shown that an image of defects within a solid material could be successfully restored by MCRW image method. This system and method also provide an accurate representation of the defect shape.

16 Claims, 12 Drawing Sheets

SYSTEM AND METHOD FOR ULTRASONIC IMAGE RECONSTRUCTION USING MODE-CONVERTED RAYLEIGH WAVE

RELATED APPLICATION

This application is based on Provisional Application, Ser. No. 60/149,054, filed on Aug. 16, 2000.

BACKGROUND OF THE INVENTION

1. Field of the Invention

Determining the presence of cracks or flaws in materials and solid structures is important in many fields. In order to reliably predict failures, it is often desirable to be able to determine the size and nature of cracks inside the material through Nondestructive Evaluation (NDE) methods. However, it remains a difficult problem to accurately visualize the cracks, which can be advantageous in repairing the structure or for the implementation of future improvements.

2. Discussion of the Prior Art

Ultrasonic methods are well established in the NDE field, where ultrasonic waves are propagated through the material and the reflected surface wave, or so called "Rayleigh waves", are analyzed to determine the presence of flaws. U.S. Pat. No. 5,894,092 to Lindgren, et al, for example, teaches a method for obtaining near-surface characteristics of a material through the generation of a series of single frequency Rayleigh waves, detecting the reflected Rayleigh waves and determining their velocities in order to obtain the depth from the surface of one or more characteristics of the material. U.S. Pat. No. 5,974,889 to Trantow, on the other hand, discloses a method for ultrasonically scanning a surface with a ultrasonic waves from an apparatus comprising a plurality of transducers to detect characteristics on a material's surface. The inventor of the present invention was one of the named inventors of U.S. Pat. No. 5,859,370, granted on Jan. 12, 1999 (hereinafter "the '370 patent"). The '370 patent discloses a method of detecting and sizing small cracks in roots between crests in stud bolt threads. The '370 patent is hereby incorporated herein in its entirety. It teaches a method comprising the steps of radiating an ultrasonic wave into the flank of the bolt threads, detecting the reflected signal which is one of the regularly spaced signals reflected from the threads, detecting a Rayleigh wave signal from the Rayleigh wave propagating along the crack, measuring the elapsed time from the reflected signal and ending at the Rayleigh wave signal, and calculating the crack size by the elapsed time. Digital signal processing means, including modified wave shaping, dynamic predictive deconvolution and a combination thereof, are utilized to efficiently detect the Rayleigh waves. By this method, a crack as small as 1–2 mm can be detected inside a material.

In conventional ultrasonic imaging methods, the specular reflections are usually used for image reconstruction. However, these techniques are not efficient in most cases due to multiple specular reflections or mode converted acoustic waves, resulting in a distorted or inaccurate image that is not representative of the crack. In conventional methods, the resolution is often poor as the wavelength of the ultrasonic signal approaches the dimensions of the defect. This would occur when the defect sought to be imaged is very small. It is a goal of the present invention to obtain higher resolution and higher accuracy in the reconstructed image than possible with conventional methods through the use of Mode Converted Rayleigh Waves (MCRW).

SUMMARY OF THE INVENTION

In the present invention, a ultrasonic signal transmitter and an array of signal receivers are utilized to measure cracks and flaws within a solid material. MCRW is used for ultrasonic image reconstruction and the specular reflection is used for range reference in the image. To effectively detect the MCRW, small aperture transducers are used and the transducers are circularly arranged around the transmitter. In addition, deconvolution methods are used to suppress the effect of specular echo on the MCRW.

BRIEF DESCRIPTION OF THE DRAWINGS

FIG. 1. Schematic showing the Mode Converted Rayleigh Wave method: (a) wave paths of the transmitted and reflected waves, (b) specular reflection signals obtained by pulser/echo method, (c) Rayleigh wave signals obtained by pitch/catch method, (d) arrangement of the transducer array in a circular pattern, (e) steel block sample with a flat bottom hole and (f) wave pattern of the reflected waves from the flat bottom hole.

FIG. 2. Schematic showing (a) Pulser/echo method (use of one transducer for both sending and receiving the signal) and (b) Pitch/catch method (use of more than one transducer, one for sending and at least one more for receiving signals).

FIG. 3. Ultrasonic signals from the flat bottom hole sample (2.0 mm diameter): (a) specular ultrasonic signals and (b) Rayleigh wave signals.

FIG. 7. Reconstructed MCRW images by applying MCRW image technique to the signals in FIG. 3(b): (a) a 2-D MCRW image by deconvolution technique and (b) a 3-D MCRW image by deconvolution technique.

DETAILED DESCRIPTION OF THE INVENTION

This invention makes use of transducers to propagate ultrasonic waves through a solid material and analyzing the reflected Mode Converted Rayleigh Waves (MCRW) from flaws present in the material in order to detect the presence of such flaws, and to apply MCRW imaging methods to accurately re-construct an image of the flaw.

Figure 1A:
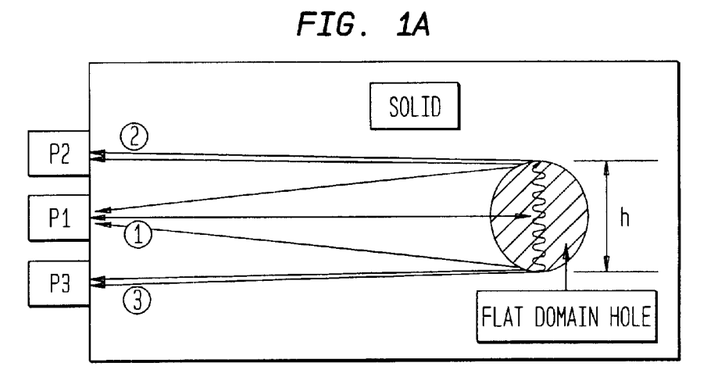
Figure 1B:
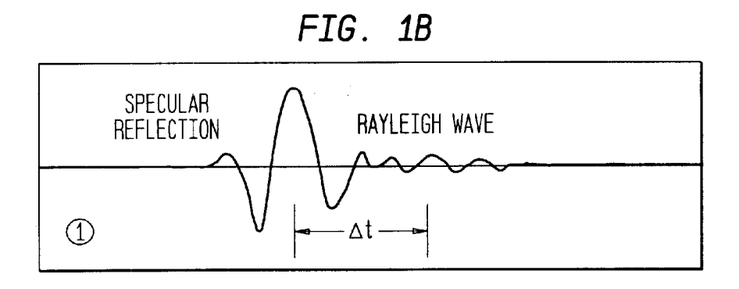
Figure 1C:
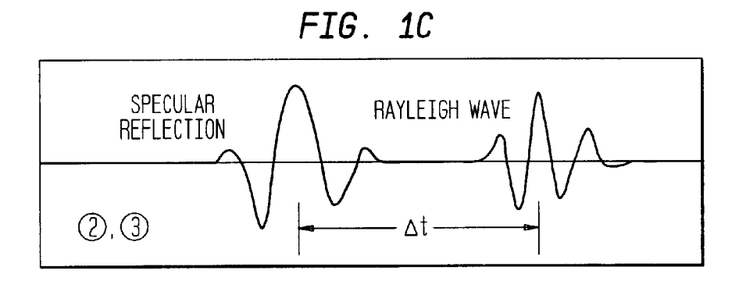
Figure 2A:
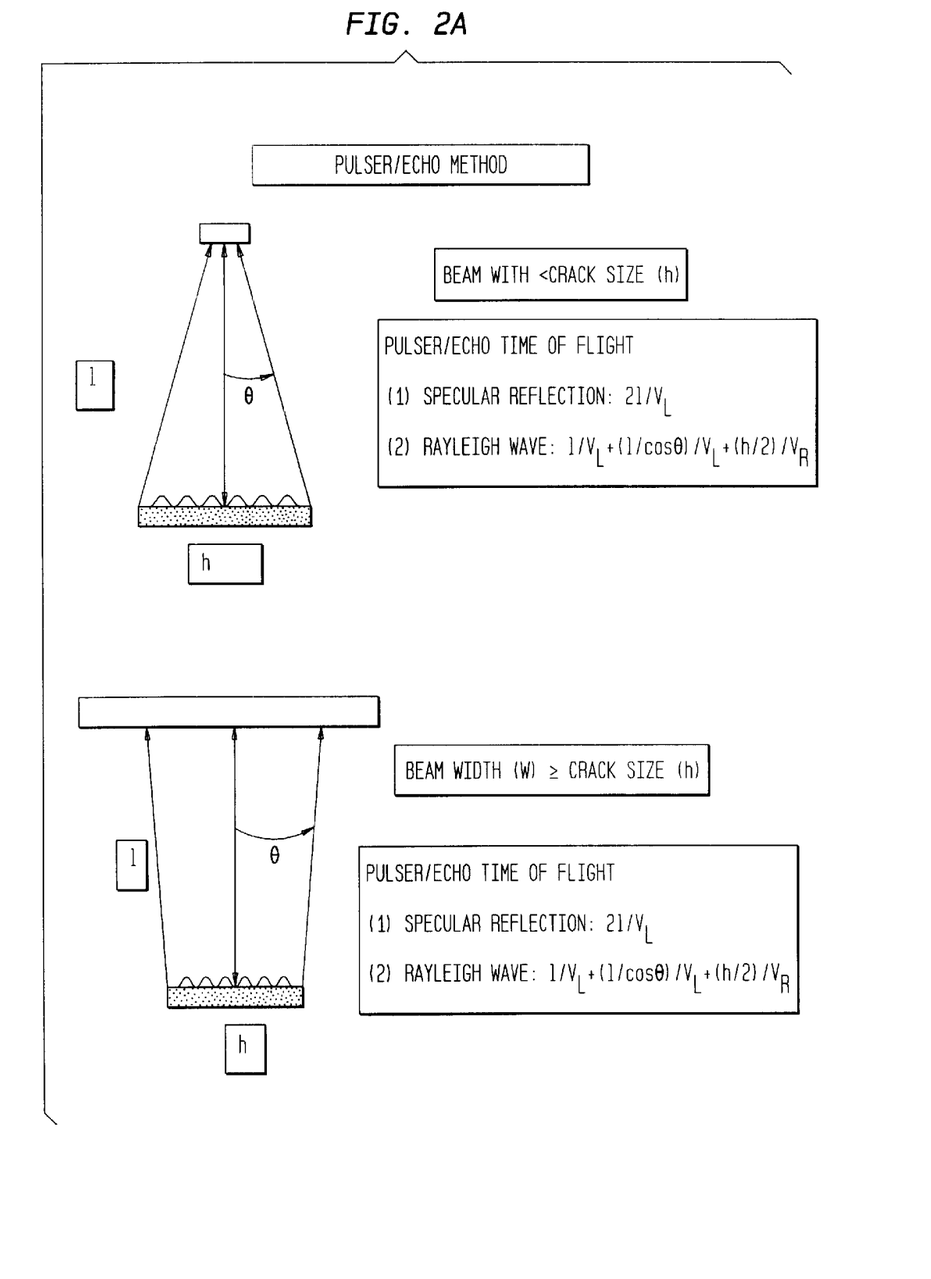
Figure 2B:
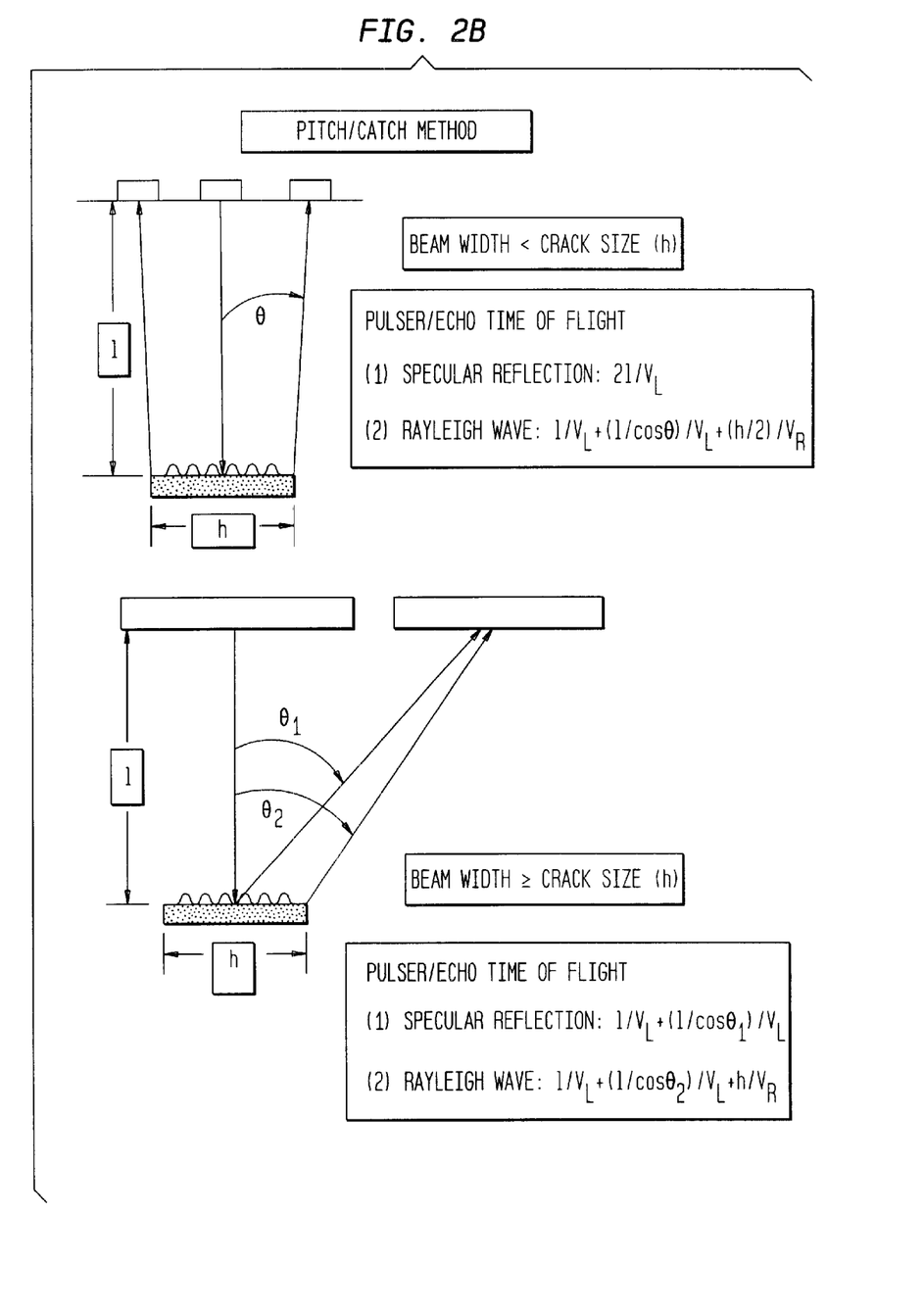

FIG. 1(a) schematically shows the Rayleigh wave method for crack sizing and detection. It is assumed that the distance of the transducer to the crack is larger compared with the height (or diameter) of the crack (in this example a flat bottom hole ("FBH")), and that the beam width of transducer is narrow. Also, the incident beam is assumed to be perpendicular to the crack surface. The incident beam propagates through the solid material and is reflected at the crack. Using a pulse/echo method (see FIG. 2(a)), the signals received at the transducer P1 would be: the specular reflection and the trailing Rayleigh wave signals (FIG. 1(b)). As FIG. 1(b) shows, the pulse/echo signals would be dominated by a specular refection from the center of the FBH face. The Rayleigh wave signals would be very small compared with the specular reflection signals and, in many cases, they would not be readily distinguished. Using the pitch/catch method (see FIG. 2(b)), FIG. 1(c) shows the signal that would be received at the transducer P2 (or P3). The first echo would be the specular reflection. The second echo would be the Rayleigh wave which travels from the center of the crack to the edge along the surface and turns 90 degrees to the transducer. See FIG. 1 (f). (It is assumed that the beam width is narrower than the crack diameter.)

Figure 1D:
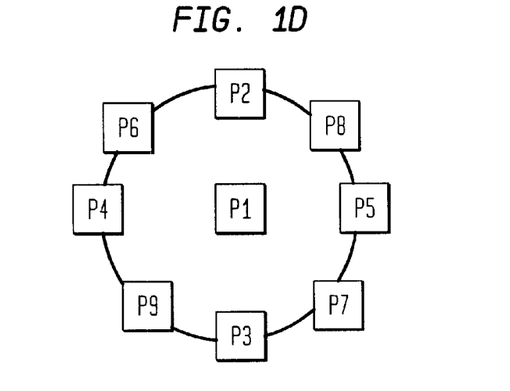

By comparing FIG. 1(b) and FIG. 1(c), it is clear that the transducers need to be arranged appropriately to separate the Rayleigh wave signal from the specular echo signals. In this example, the transducers are arranged as shown in FIG. 1(d) where P1 is the transmitter and P2~Pn are receivers. In FIG. 1(c), Δt is defined as the delay time between the specular signal and the Rayleigh wave signal. It can be shown that Δt is given by $$\Delta t = \frac{h}{2V_R}$$

where $V_R$=Rayleigh wave velocity and h=diameter (height) of the crack face. Rayleigh wave velocities of materials are readily discernible (for example, it is 2900 m/sec in steel, approximately 92% of transverse wave velocity).

Figure 1E:
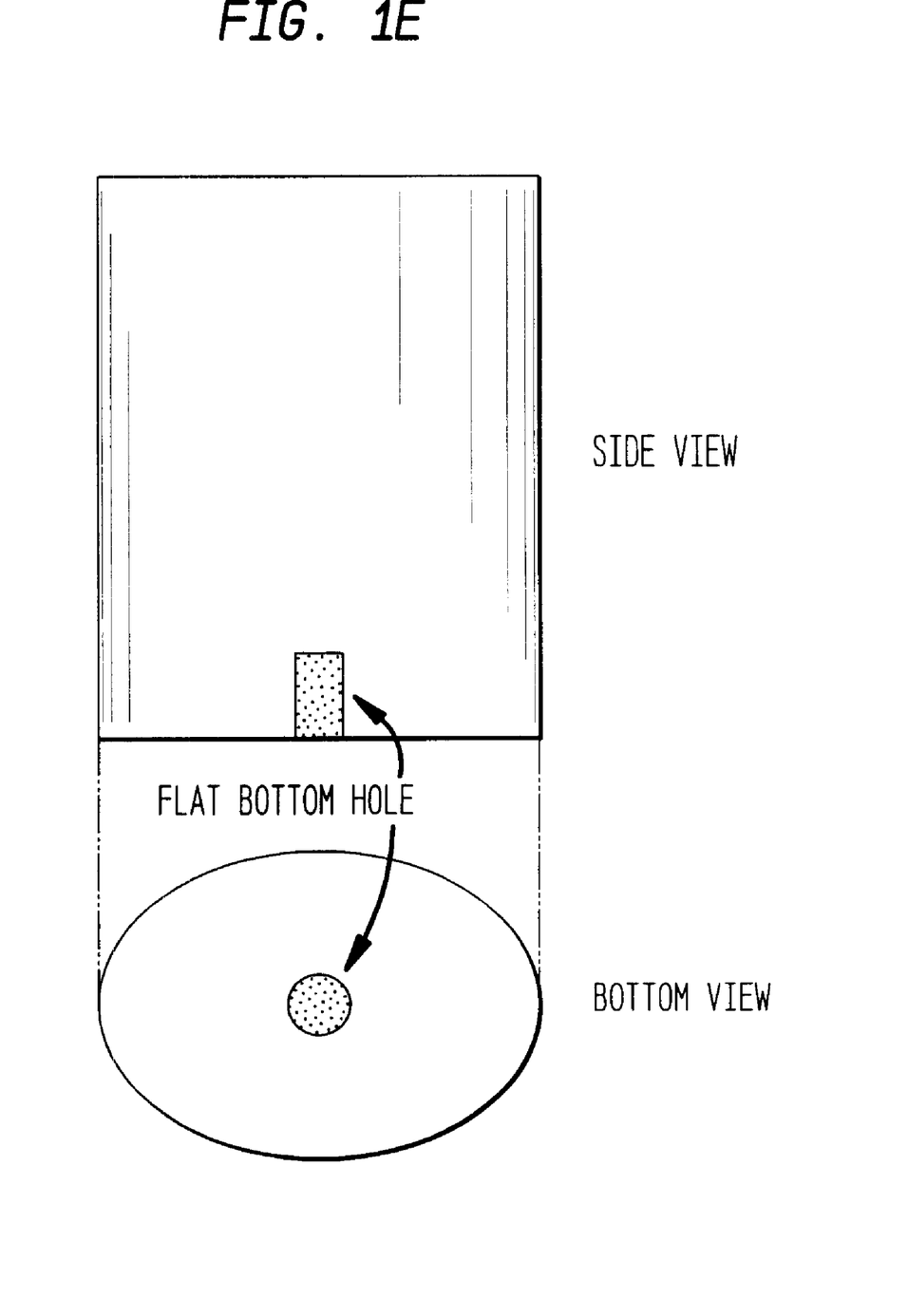
Figure 1F:
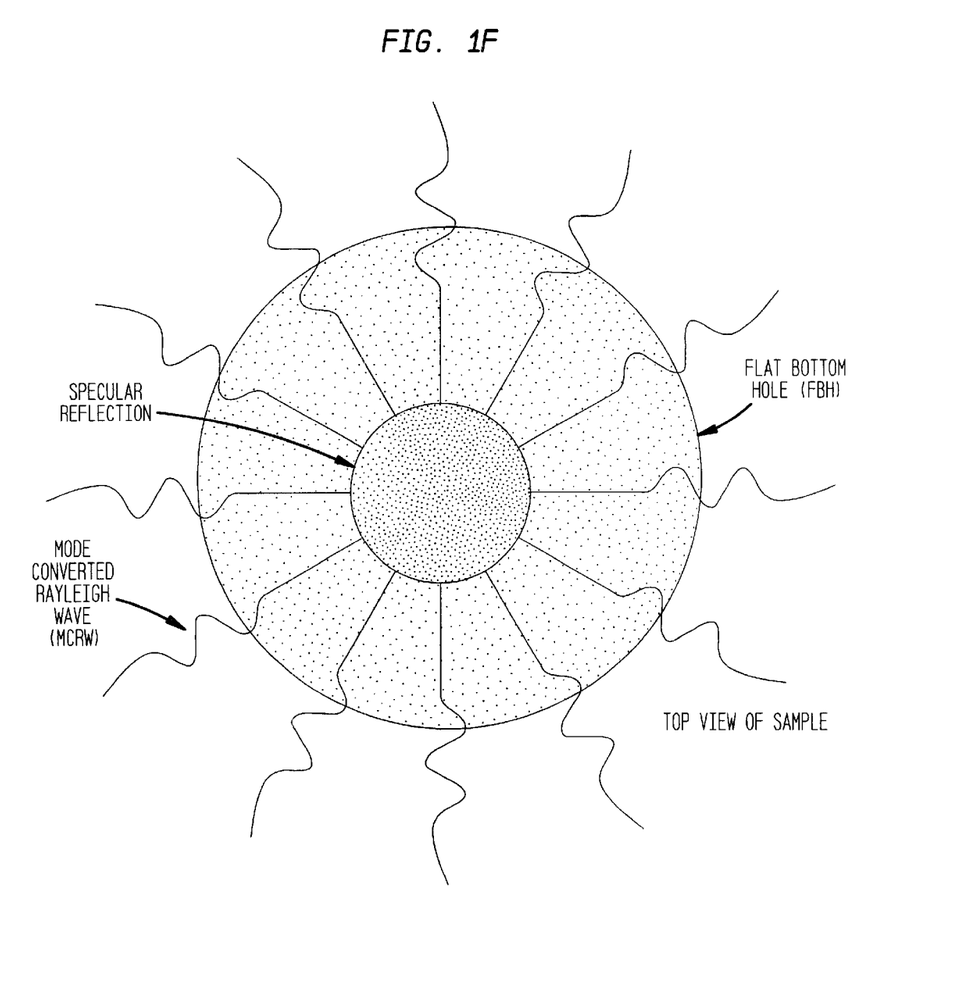

To verify the above, a carbon steel test specimen with a FBH (diameter 2.0 mm) was fabricated (Trienco Inc. 4340-5-0025 steel block). See FIG. 1(e). The FBH is encased within the sample and is undetectable to the eye from the top side. This experiment will show that the invention can detect the presence of the FBH through the solid block and reconstruct an image of the FBH by the MCRW imaging method.

Figure 3A:
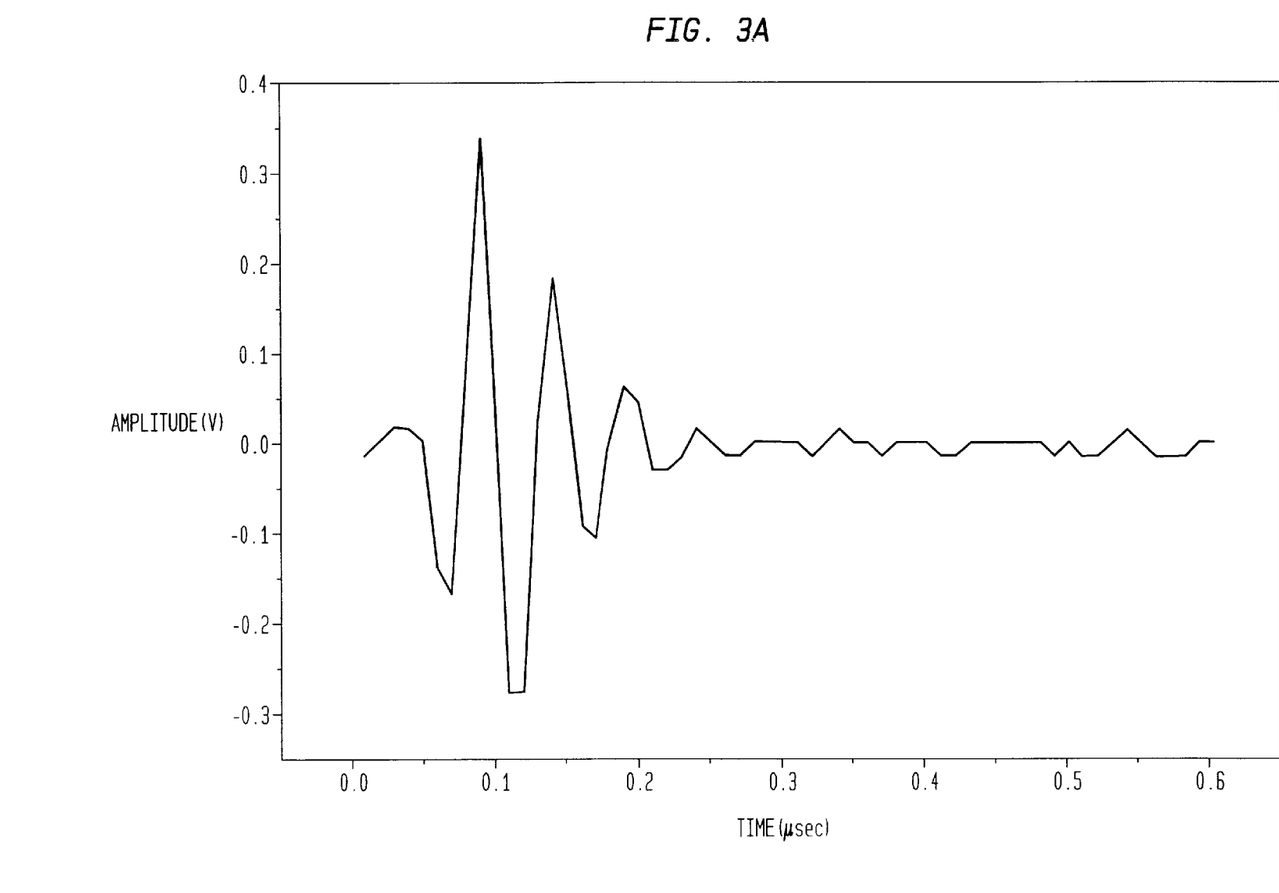
Figure 3B:
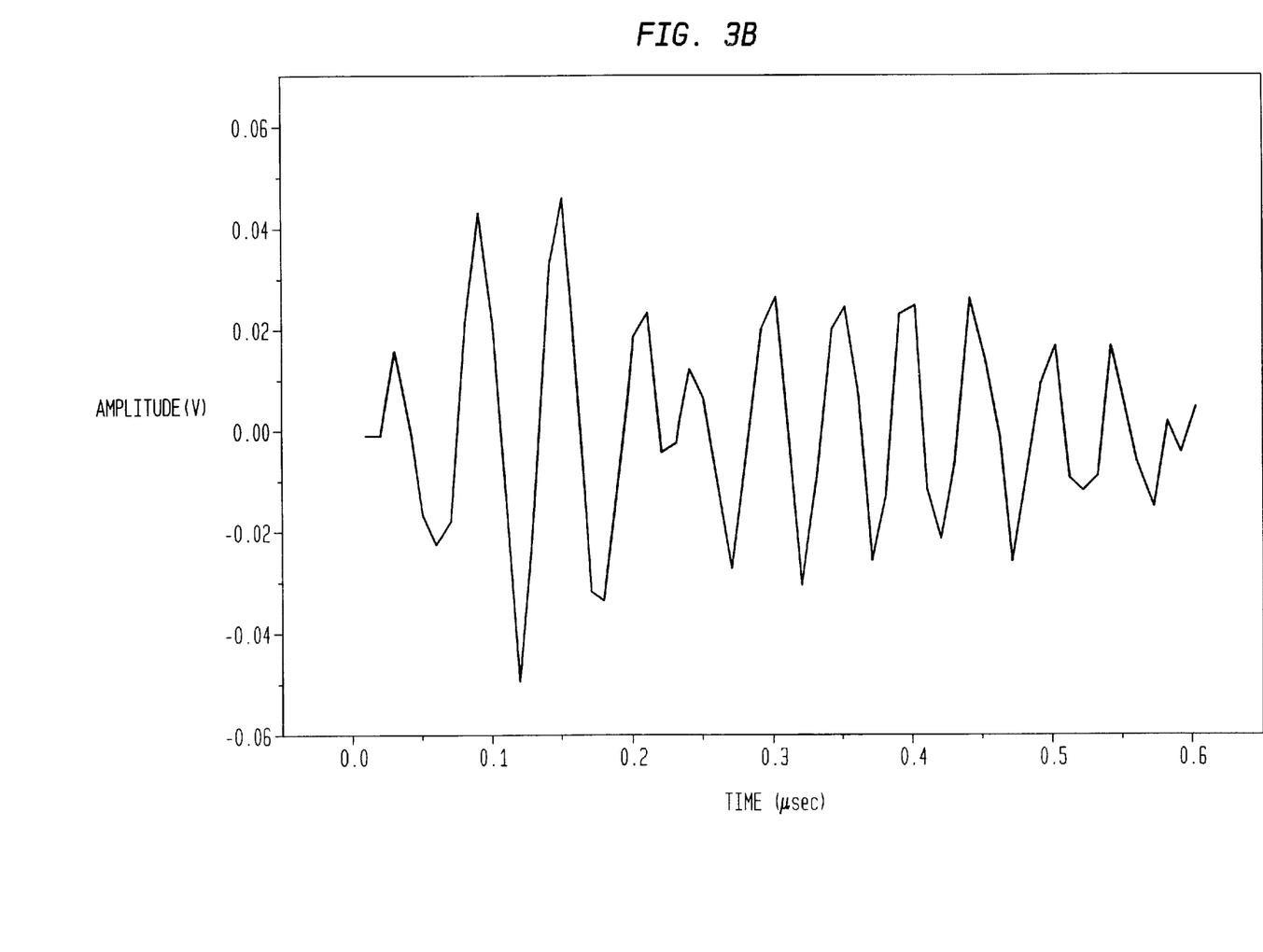
Figure 4:
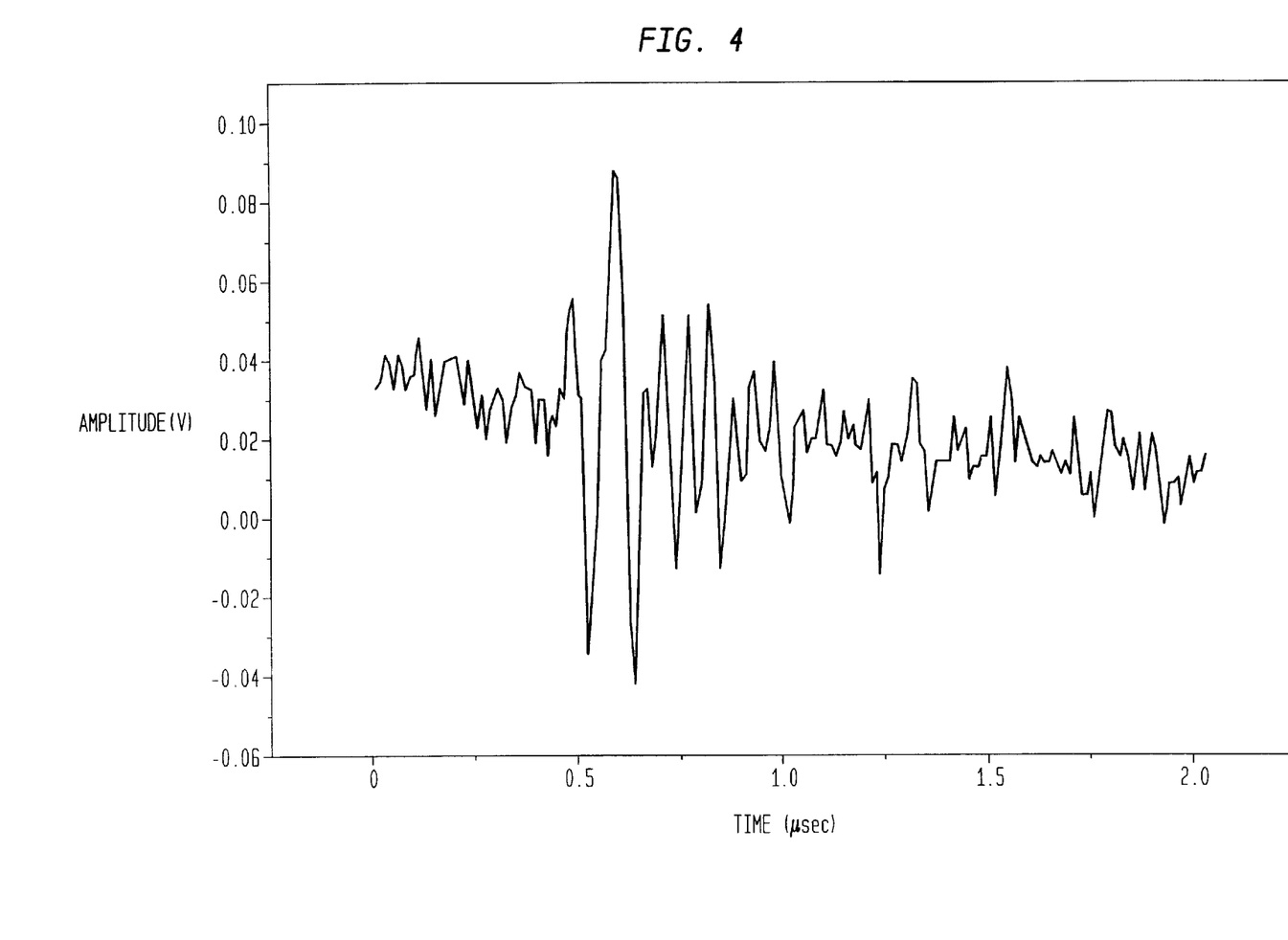
FIG. 4. Ultrasonic signal obtained by pitch/catch method from 2.0 mm diameter flat bottom hole with 10 MHz transducer.

The experiment was carried out using Panametrics Model 5601A Pulser/Recievers as the transducers, which were placed at the side of the sample furthest away from the FBH. The transducer emitted a pulse through the sample and the reflected signals received were mapped on a Lecroy 9310 digital oscilloscope. FIG. 3(a) shows the display readout of the oscilloscpe of the signals obtained by a pulser/echo method from the FBH with a 10 MHz transducer. As can be seen from FIG. 3(a), it is difficult to differentiate the Rayleigh wave from the specular reflection wave. FIG. 3(b) shows the display readout of the signals obtained by pitch/catch method, again with 10 MHz transducers. The signals reflected from the FBH are the specular reflections and the trailing Rayleigh wave signals. By way of another example, another signal obtained from a pitch/catch method (FBH diameter 2 mm: Trienco Inc. 4340-5-0038 steel block) by 10 MHz transducers is shown in FIG. 4. As can be seen from FIG. 3(b) and FIG. 4, the Rayleigh wave can be easily differentiated from the specular reflection wave if the signal is collected by pitch/catch method.

Using the results from above, the image is reconstructed by utilizing MCRW as follows:

1. The highest specular echo from the center of reflector surface is arranged at the image center.
2. Each Rayleigh wave received by the circularly-arranged receivers is processed by deconvolution.
3. Each Rayleigh wave from step 2 is perpendicularly arranged to the image center (MCRW is orthogonal to the axial beam direction).

Unlike conventional methods which uses the specular reflection for image reconstruction, the method only uses the specular reflection as the range reference for the image.

Figure 5:
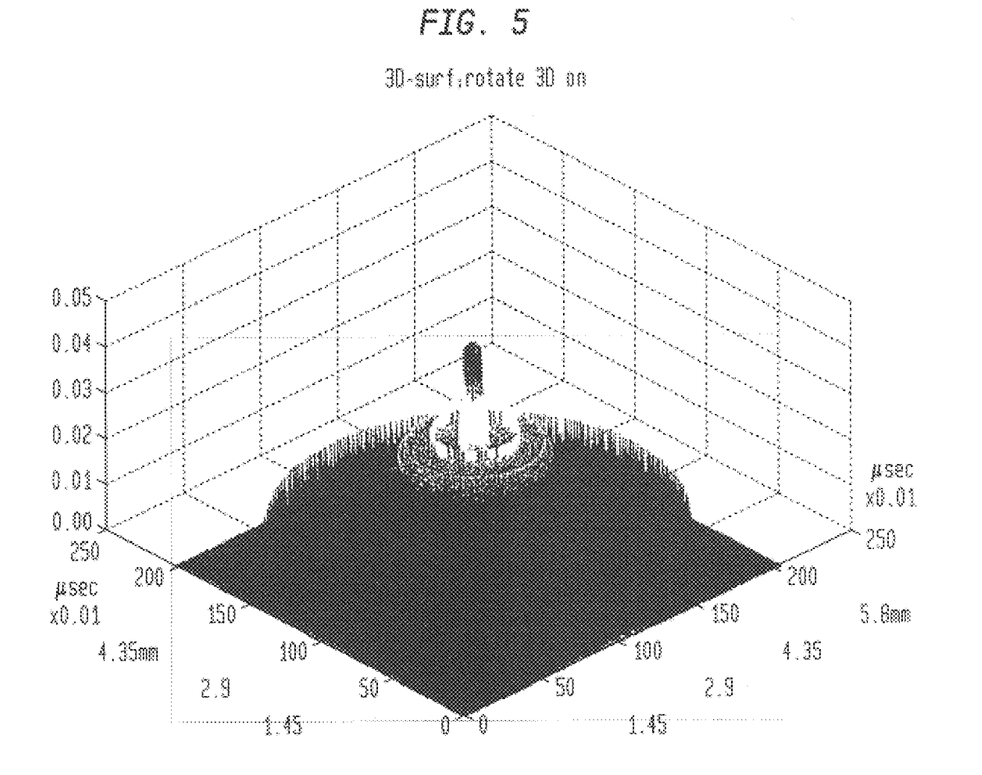
FIG. 5. Reconstructed image by applying MCRW image technique to the signal of FIG. 3 (b).

To show the validity of the proposed method, test specimens with flat bottom holes are tested with 5 MHz and 10 MHz array transducers. To obtain the MCRW image, transducers are arranged circularly as shown in FIG. 1(d). FIG. 5 is the MCRW image obtained by the pitch/catch signals from the FBH. In this image, the strongest specular echo is arranged at the center of the image and the Rayleigh wave signals are arranged circularly by 10 degrees angle increment. In this figure, the region of interest is 2 mm wide. The image quality can then be improved significantly by using a deconvolution technique as follows.

To enhance the MCRW image, it is important to minimize and isolate the effect of the specular echo on the MCRW signal. In this section, it is shown that a deconvolution technique can be used to suppress the effect of specular echo on MCRW.

Given a reference signal a(n), we want to find a mathematical operator f(n) that will transform a(n) into a desired waveform d(n) by the convolution of a(n) with f(n), i.e., $$d(n)=a(n)*f(n),$$

where (*) means the convolution operation. However, the finite length of f(n) will introduce errors and consequently the waveform computed by the convolution of a(n) with the finite-length f(n) is not equal to the desired waveform d(n). The optimum operator f(n) with the length of m+1 can be obtained by solving the following equation $$\sum_{s=0}^{m} f_s r_{j-s} = g_j, \quad j=0, 1, \ldots, m,$$

where $$r_{j-s} = \sum_{n=0}^{m} a(n-s)a(n-j),$$

$$g_j = \sum_{n=0}^{m} d(n)a(n-j).$$

Notice that $r_{j-s}$ is the autocorrelation of a(n) and $g_j$ is the correlation of d(n) with a(n). Thus, the optimized coefficients off f(n) can be obtained by solving the following matrix equation:

$$\begin{bmatrix} r_0 & r_1 & \cdots & r_m \\ r_1 & r_0 & \cdots & r_{m-1} \\ \vdots & \vdots & \vdots & \vdots \\ r_m & r_{m-1} & \cdots & r_0 \end{bmatrix} \begin{bmatrix} f(0) \\ f(1) \\ \vdots \\ f(m) \end{bmatrix} = \begin{bmatrix} g_0 \\ g_1 \\ \vdots \\ g_m \end{bmatrix}$$

The minimized error will then be $$E_{\min} = \sum_{n=0}^{\infty} d(n)^2 - \sum_{n=0}^{\infty} f(n)g(n)$$

In our method, the specular reflection signal obtained with a pulser/echo method (e.g., the signal in FIG. 3(a)) is used as the reference signal. Also, zero is chosen to be the desired signal. Of course, the operator f(n) should be nonzero.

Figure 6:
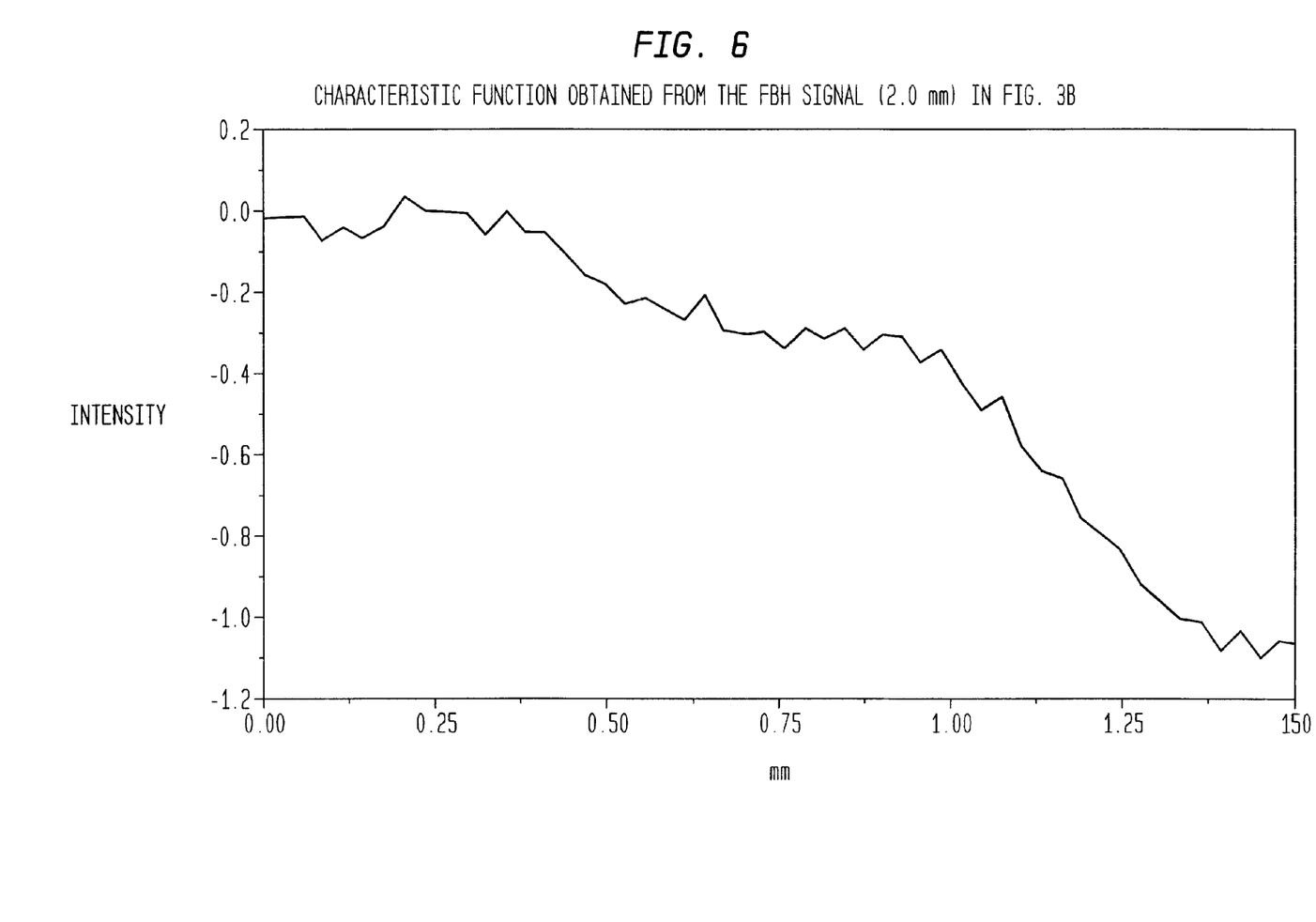
FIG. 6. Characteristic function obtained from the signal of FIG. 3(b).
Figure 7A:
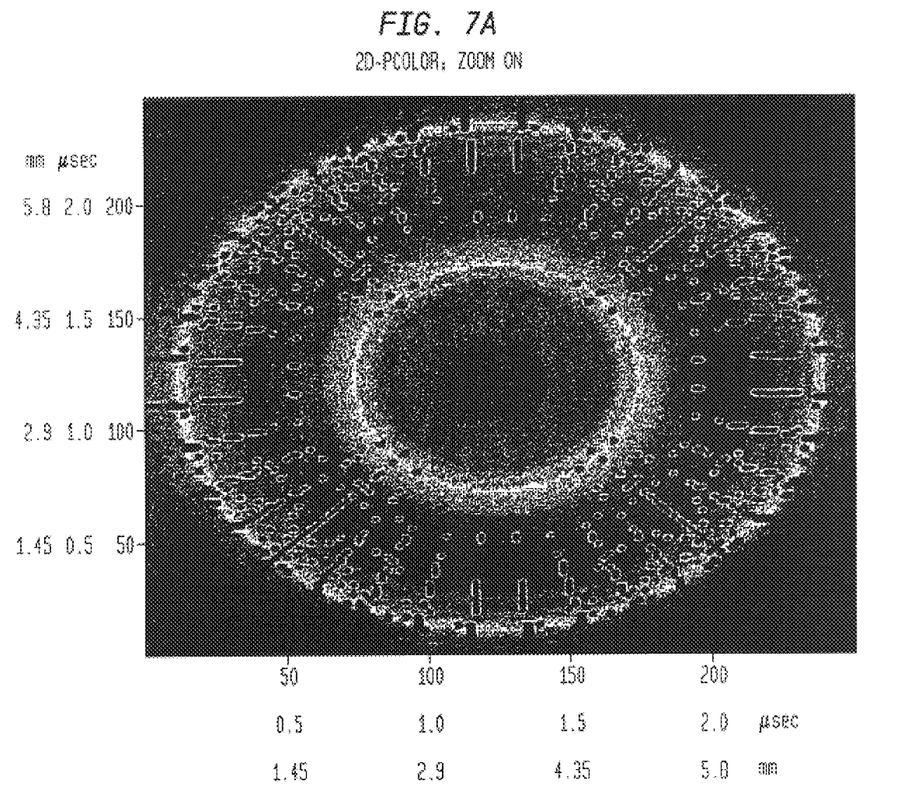
Figure 7B:
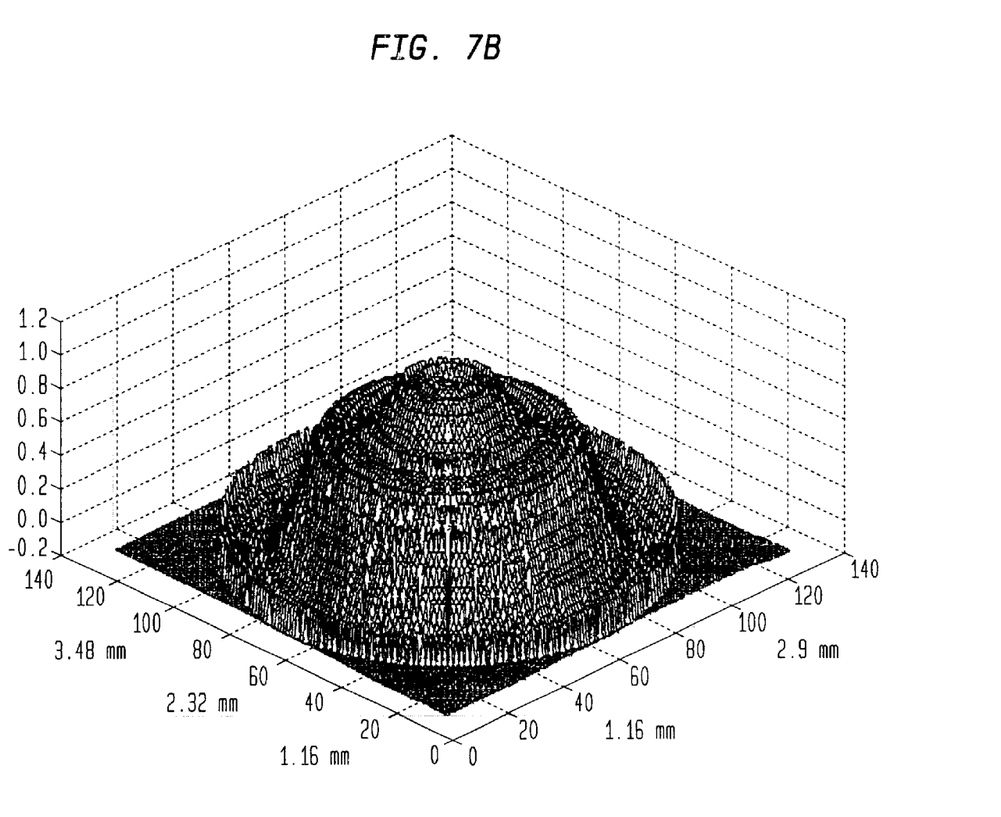

By applying the operator to the signal in FIG. 3(b), the restored signal is obtained as shown in FIG. 6. From FIG. 6, 2- and 3-dimensional FBH images created by the MCRW image method are obtained as shown in FIG. 7. The measured time delay Δt is 0.35 μsec (50% of the peak value in FIG. 6). When it is assumed the velocity of Rayleigh wave is 2.9 mm/μsec in the steel, the FBH size is estimated to be 2 mm (2.9 mm/μsec×0.35 μsec×2). By this method, the defect size is successfully predicted.

It is understood that the present invention is able to reconstruct the image of flaws that are irregular, and not just the circular FBH used in the experiment.

What is claimed is:

1. A method for reconstructing an image of a defect embedded in a solid material, comprising the steps of:

setting a plurality of ultrasonic transducers on the solid material;

radiating an ultrasonic wave into the solid material;

detecting reflected waves by the ultrasonic transducers, said reflected waves comprising specular waves reflected from the defect, and Rayleigh waves propagating along the surface of the defect and reflected at the edge of said defect;

mapping the reflected waves detected to waveforms;

arranging the highest specular waveform from the specular wave reflected from the center of the defect surface as the center of the reconstructed image of the defect; and arranging each Rayleigh waveform perpendicularly to the center of the reconstructed image.

2. The method of claim 1, wherein the plurality of transducers are small aperture transducers circularly arranged around a ultrasonic wave transmitter.

3. The method of claim 1, wherein the reconstructed image of the defect is two-dimensional.

4. The method of claim 1, wherein the reconstructed image of the defect is three-dimensional.

5. A method for reconstructing an image of a defect embedded in a solid material, comprising the steps of:

setting a plurality of ultrasonic transducers on the solid material;

radiating an ultrasonic wave into the solid material;

detecting reflected waves by the ultrasonic transducers, said reflected waves comprising specular waves reflected from the defect, and Rayleigh waves propagating along the surface of the defect and reflected at the edge of said defect;

mapping the reflected waves detected to waveforms;

applying deconvolution to each Rayleigh waveform to obtain deconvoluted Rayleigh waveforms;

arranging the highest specular waveform from the specular wave reflected from the center of the defect surface as the center of the reconstructed image of the defect; and arranging each deconvoluted Rayleigh waveform perpendicularly to the center of the reconstructed image.

6. The method of claim 5, wherein the plurality of transducers are small aperture transducers circularly arranged around a ultrasonic wave transmitter.

7. The method of claim 5, wherein the reconstructed image of the defect is two-dimensional.

8. The method of claim 5, wherein the reconstructed image of the defect is three-dimensional.

9. A system for the reconstruction of an image of a defect embedded in a solid material, comprising:

means for radiating an ultrasonic wave into the solid material;

means for detecting reflected waves by the ultrasonic transducers, said reflected waves comprising specular waves reflected from the defect, and Rayleigh waves propagating along the surface of the defect and reflected at the edge of said defect;

means for mapping the reflected waves detected to waveforms;

means for arranging the highest specular waveform from the specular wave reflected from the center of the defect surface as the center of the reconstructed image of the defect;

means for arranging each Rayleigh waveform perpendicularly to the center of the reconstructed image; and means for displaying the reconstructed image.

10. The system of claim 9, wherein the means for radiating an ultrasonic wave into the solid material are a plurality of small aperture transducers.

11. The system of claim 9, wherein the reconstructed image of the defect is two-dimensional.

12. The system of claim 9, wherein the reconstructed image of the defect is three-dimensional.

13. A system for the reconstruction of an image of a defect embedded in a solid material, comprising:

means for radiating an ultrasonic wave into the solid material;

means for detecting reflected waves by the ultrasonic transducers, said reflected waves comprising specular waves reflected from the defect, and Rayleigh waves propagating along the surface of the defect and reflected at the edge of said defect;

means for mapping the reflected waves detected to waveforms;

means for applying deconvolution to each Rayleigh waveform to obtain deconvoluted Rayleigh waveforms;

means for arranging the highest specular waveform from the specular wave reflected from the center of the defect surface as the center of the reconstructed image of the defect;

means for arranging each Rayleigh waveform perpendicularly to the center of the reconstructed image; and means for displaying the reconstructed image.

14. The system of claim 13, wherein the means for radiating an ultrasonic wave into the solid material are a plurality of small aperture transducers.

15. The system of claim 13, wherein the reconstructed image of the defect is two-dimensional.

16. The system of claim 13, wherein the reconstructed image of the defect is three-dimensional.

* * * * *